US007425453B1

United States Patent
Hutchens et al.

(10) Patent No.: US 7,425,453 B1
(45) Date of Patent: Sep. 16, 2008

(54) INTEGRATED CIRCUIT PORPHYRIN-BASED OPTICAL FABRY-PEROT CHEMICAL SENSOR

(75) Inventors: Chris Hutchens, Stillwater, OK (US); Richard L. Waters, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 880 days.

(21) Appl. No.: 10/763,133

(22) Filed: Jan. 22, 2004

Related U.S. Application Data

(63) Continuation-in-part of application No. 10/245,617, filed on Sep. 17, 2002, now Pat. No. 6,763,718, which is a continuation-in-part of application No. 09/892,301, filed on Jun. 26, 2001, now Pat. No. 6,546,798, which is a continuation-in-part of application No. 09/808,570, filed on Mar. 14, 2001, now Pat. No. 6,581,465.

(51) Int. Cl.
*G01N 21/01* (2006.01)
*G01N 21/27* (2006.01)
*G01N 33/00* (2006.01)
*G01J 3/26* (2006.01)

(52) U.S. Cl. .................. 436/165; 356/454; 422/82.05; 422/82.09; 422/86; 422/91; 436/104; 436/111; 436/113; 436/120; 436/131; 436/132; 436/139; 436/164; 436/167; 436/171

(58) Field of Classification Search ................. 250/343, 250/345, 364, 366, 373; 356/454; 422/82.05, 422/82.09, 86, 91; 436/104, 111, 113, 120, 436/131–132, 139, 164–165, 167, 171
See application file for complete search history.

(56) References Cited

U.S. PATENT DOCUMENTS 4,859,060 A * 8/1989 Katagiri et al. ............. 356/454
(Continued)

OTHER PUBLICATIONS

Rakow, N. A.;Suslick, K.S. "A Colorimetric Sensor Array for Odour Visualization" Nature 2000, vol. 406, 710-714.
(Continued)

*Primary Examiner*—Arlen Soderquist
(74) *Attorney, Agent, or Firm*—Kyle Eppele; Peter A. Lipovsky; J. Eric Anderson

(57) ABSTRACT

A Fabry-Perot cavity has a pair of partially transmissive, partially reflective, surfaces. A first of the surfaces is flexibly suspended adjacent and parallel to a second of the surfaces. A gap exists between the surfaces. A variable electrostatic potential permits this gap to be adjusted. A translucent chemical layer is disposed on the first surface. A photosensor is attached to the second surface. Light irradiates the photosensor through the chemical layer and the first and second surfaces wherein the light is also partially reflected between the surfaces. A sensing environment is provided wherein an agent undergoes a reaction with the chemical layer as well as an environment wherein the reaction does not occur. The output of the photosensor is measured to assess a change in spectrum and spectral intensity for each of the sensing environments. The gap between the surfaces as well as the light used are selected to provide an optimum photosensor output.

19 Claims, 2 Drawing Sheets

U.S. PATENT DOCUMENTS

| | | | | |
|---|---|---|---|---|
| 4,945,230 A | * | 7/1990 | Saaski et al. | 250/227.21 |
| 5,437,840 A | * | 8/1995 | King et al. | 422/82.08 |
| 5,591,407 A | * | 1/1997 | Groger et al. | 422/82.05 |
| 5,818,586 A | * | 10/1998 | Lehto et al. | 356/454 |
| 5,867,267 A | * | 2/1999 | Benech et al. | 356/477 |
| 6,078,395 A | * | 6/2000 | Jourdain et al. | 356/519 |
| 6,649,403 B1 | * | 11/2003 | McDevitt et al. | 435/288.5 |

OTHER PUBLICATIONS

Waters, Richard, et al. Micromechanical Optoelectronic Switch and Amplifier (MIMOSA) Selected Topics in Quantum Electronics, IEEE Journal on vol. 5, Issue 1 Jan.-Feb. 1999.

Elsevier, Sensing of biological substances based on the bending of microfabricated cantilevers, Sensors and Actuators B chemical, Sensors and Actuators B 61 (1999) 213-217. 1999 Elsevier Science B.V. all rights Reserved. www.elsevier.nl/locate/sensorb.

Chou, J.-H.; Kosal, M.E.; Nalwa, H.S.; Rakow, N.A. Suslick S.S. "Applications of Porphyrins and Metalloporphyrins to Materials Chemistry" The Porphyrin Handbook, Academic Press 2000, vol. 6, Ch. 41, pp. 43-131.

* cited by examiner

INTEGRATED CIRCUIT PORPHYRIN-BASED OPTICAL FABRY-PEROT CHEMICAL SENSOR

RELATED APPLICATIONS

This application is a continuation-in-part of U.S. patent application Ser. No. 10/245,617, filed Sep. 17, 2002, now U.S. Pat. No. 6,763,718, which is in turn a continuation-in-part of U.S. patent application Ser. No. 09/892,301, filed Jun. 26, 2001, now U.S. Pat. No. 6,546,798, which is a continuation-in-part of U.S. patent application Ser. No. 09/808,570, filed Mar. 14, 2001, now U.S. Pat. No. 6,581,465. This application is also related to U.S. Pat. No. 6,550,330.

BACKGROUND

The ensuing description relates generally to sensing systems.

SUMMARY

A technique of sensing comprises a Fabry-Perot cavity having pair of partially transmissive, partially reflective, surfaces. A first of the surfaces is flexibly suspended adjacent and parallel to a second of the surfaces so that a gap exists therebetween. A source of variable electrostatic potential is provided to allow a selected electrostatic potential to exist between the first and second surfaces, permitting the gap between the surfaces to be adjusted.

A translucent chemical layer, such as porphyrin, is disposed upon the flexibly suspended first surface. A photosensor is attached to the second surface. A light source provides light to irradiate the photosensor through the chemical layer and the first and second surfaces wherein the light is also partially reflected between the surfaces.

A sensing environment is provided wherein an agent undergoes a reaction with the chemical layer. A sensing environment wherein the reaction does not occur is also provided to create a reference condition. These two environments can be provided separately or simultaneously.

The output of the photosensor is measured to assess a change in spectrum and spectral intensity for each of the sensing environments. The gap between the partially transmissive and partially reflective surfaces as well as the light used are selected to provide an optimum photosensor output.

Other objects, advantages and new features will become apparent from the following detailed description when considered in conjunction with the accompanied drawings.

DESCRIPTION

Figure 1A:
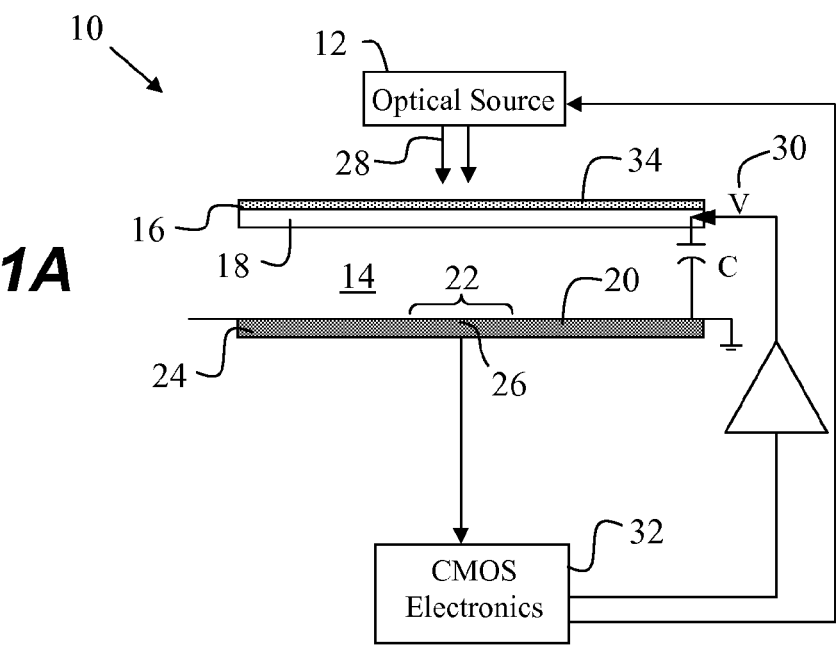
FIG. 1A is a cross-section view of a representative sensor according to the description herein.

Referring to now FIG. 1A, a representative sensor 10 is shown. Aspects of sensor 10 lend themselves to being fabricated according to well-understood steps familiar to the semiconductor processing field and the micro-electro-mechanical systems (MEMS) world, enabling the sensor to be easily manufactured as an integrated circuit.

Sensor 10 uses an optical source 12 such as a band-limited or tunable wavelength monochromatic solid state laser. This light is coupled directly or indirectly, such as via fiber-optic cable, to a Fabry-Perot cavity 14.

The Fabry-Perot cavity is the optical cavity between upper and lower mirrors. In this case, a first or upper mirror 16 of the cavity is formed on a surface of a hinged membrane 18 that is flexibly suspended above and substantially parallel to a second or lower mirror 20. Upper mirror 16 is designed to partially reflect and partially transmit light from and into cavity 14. This mirror can be a conductive layer, such as doped silicon, or a thin semi-transparent metalization, for example gold, that is located on the top surface of membrane 18. Lower mirror 20 exists on the surface of a $p^+$ region 22 created in substrate 24 which, for example, is of silicon. Mirror 20 can be made for example by the semiconductor/air interface or via the deposition of a thin semi-transparent metal on the surface of region 22. Both mirrors 16 and 20 can also be fabricated through the deposition of various dielectric layers, known as a dielectric stack, to form a dielectric mirror at a desired wavelength. In the dielectric stack embodiment, a thin conducting layer deposited either between the layers of the dielectric stack or on a surface of the stack form an electrode for electrostatic actuation.

The $p^+$ region 22 and n substrate 24 create a $p^+n$ junction photosensor (photodiode) shown at 26 used to absorb light 28. Photosensors of other configuration may be used such as the photodiodes of $n^+p$, pin and Schottky diode configuration, for example, as well as charged coupled device (CCD) technology.

The hinged, suspended, upper mirror 16 and attached membrane 18 can be displaced to adjust gap 14 between mirrors 16 and 20 by the application of a voltage 30. Such tuning takes place via the tuning capacitor created by the upper mirror conductive layer and the lower substrate, typically of silicon. Adjusting gap 14 permits an optimum tuning of the photo-response as received at photosensor 26.

Control 32 contains conventional spectral analyzer electronics that permit at least an analysis of light spectrum and light intensity. The control also utilizes conventional electronics to enable voltage driven cavity-gap settings as well as optical source adjustments.

All of the above components of the sensor can be fabricated as an integrated circuit (sharing a single substrate).

To enable highly focused chemical classification and/or detection, a specific translucent chemical layer or layers is/are applied to a surface of the Fabry-Perot cavity. This chemical layer is chosen to be reactive with an agent whose presence or lack of presence is desired to be known. While it is envisioned that a wide-variety of chemical layers may be used with such the cavity, a porphyrin layer including those of the category of metalloporphyrins will be further described by way of example herein.

The fundamental properties of porphyrins come from their response to macroscopic effects, including their interaction with applied fields including; electric, magnetic, or electromagnetic (EM); and with other chemical species. Here, those interactions which result in a shift in optical (EM) properties including, absorption shifts, dipole moments, and polarizability and fluorescing, are focused upon.

Figure 1B:
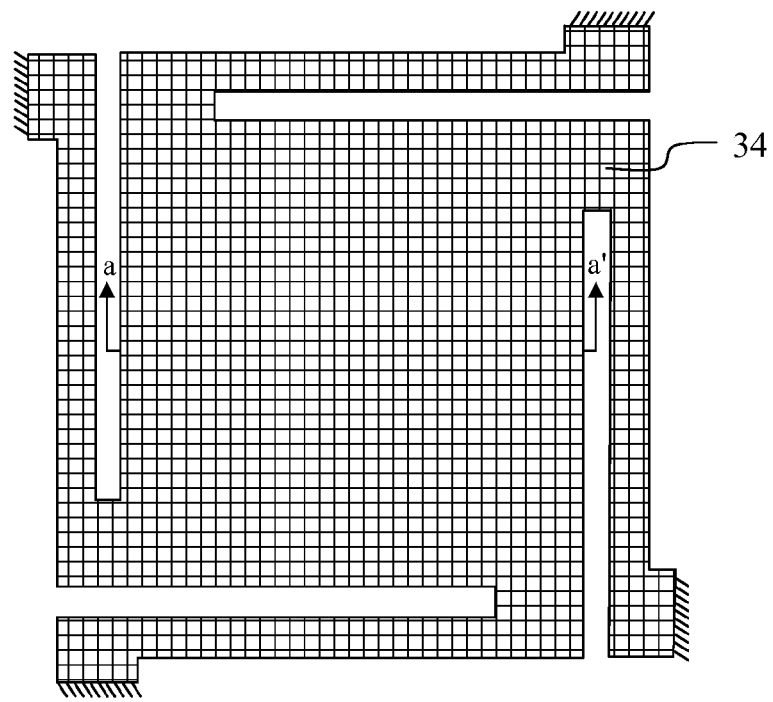
FIG. 1B depicts a top view of the representative sensor of FIG. 1A.

Referring once again to FIG. 1A, it can be seen that such a porphyrin layer 34 is shown illustrated and is perhaps more easily seen as the cross-designated area illustrated in FIG. 1B. When irradiated by an optical source, appropriately selected thin films and molecularly imprinted surfaces (MIPS) allow measurement of wavelength and intensity of absorbance, reflectance, and fluorescence.

While the agent itself is not considered to be optically detected, the optical effects of a reaction of the agent with the porphyrin layer is detectable. Such an effect can be a change in spectrophotometric characteristics, or change in mass.

It is possible to use the spectral changes of calorimetric porphyrins and related compounds (for example, metalloporphyrins, etc.) to detect a variety of agents. These compounds permit precise optical sensing, as it is known that the compounds have unique absorbencies and fluorescence spectra characteristics when reacting with specific agents, see Chou, J.-H. Et al; "Applications of Porphyrins and Metalloporphyrins to Materials Chemistry" in *The Porphyrin Handbook*, Kadish, K. et al; Academic Press: New York, 2000; vol. 6, ch. 41, pp. 43-13, and Shelnutt, J. A. (1983) "Molecular Complexes of Copper Uroporphyrin with Aromatic Acceptors"; J. of Phys. Chem. 87, 605-616.

For example, it is known that porphyrin will undergo a spectrum change upon interaction with amines arid nitro-compounds, see Del Gaudio, J. et al; (1978) J. Amer. Chem. Soc. 108, 1112-1119, and can be oxidized (ferrous porphyrin), see Castro, C. E., et al., (1986) "Ligation and Reduction of Iron (III) Porphyrins by Amines. A Model for Cytochrome P-450 Monoamine Oxidase"; J. Amer. Chem. Soc. 108, 4179-4187.

Porphyrins are known to catalyze (interact with) numerous organic molecules, see for example, Karasevich, I. E., et al., (1993) Kinetics and Catalysis 34, 651-657; Kuroda, Y., et al., (1994) Tetrahedron Letters 35, 749-750; Grinstaff, M. W., et al., (1994) Science 264, 1311-13; Banfi., S., et al., (1990) J. Chem. Soc., Chem. Commun., 1794-1796; and Battioni, P., et al., (1986) J. Chem. Soc., Chem. Commun., 341-343.

It is known that the porphyrins can be immobilized on surfaces such as semiconductors, see Traylor, T. G., et al., (1989) J. Am. Chem. Soc. 111, 8009-8010; and Aneili, P. L., et al (1989) J. Chem. Soc., Chem. Commun., 779-789 as well as quartz crystals, see Banfi, S., et al., (1991) J. Chem. Soc., Chem. Commun., 1285-1287.

Covalent immobilization has been performed by the porphyrins on surfaces reactive to side-groups of the porphyrin, for example, —COOH, —$NH_2$, —SH, or —CHO. Thiol-derived porphyrins can form a monolayer on a gold monolayer surface, see Del, Gaudio, et al., supra, on $TiC_2$ see Castro, C. E. et al., supra, and on indium-tin-oxide by spin coating, see Traylor, T. G. et al and Anelli, P. L. et al., both supra.

Metalloporphyrin has been incorporated into the cavity of a MIPS against 9-ethylamine, a nucleic acid based derivative. The absorbencies spectrum of the MIPS-based porphyrin underwent a red shift in the presence of the template (concentration-dependent) at $10^{-9}$ M levels, see Zheng, T.-C., et al., (1995) Tetrahedron Lett., 36, 833-836.

In addition, the spectral properties of porphyrins are altered by the presence of proteins, see Hennig, H., et al., (1995) Chem. Ben. 128, 229-234; nucleic acids, see Gilmartin, C., et al., (1995) J. Chern. Soc. Perkin Trans. 2, 243-251, and Shukla, R. S., et al., (1996) Journal of Molecular Catalysis A: Chemical 113, 45-49; and amino acids, see Ohtake, H., et al., (1995) Heterocycles 40, 867-903; and Appleton, A. J., et al., (1996) J. Chem. Soc. Perkins Trans 2, 281-285, with specific spectral changes for each agent.

Charge transfer ®-T) complexes between trinitrobenzene and other nitro-analogs and organics like benzene can be detected optically, see Appleton, A. J., et al., (1996) J. Chem. Soc. Perkins Trans 2, 281-285; Bolzonelia, E., et al., (1996) J. Phys. Org. Chem. 9, 539-544; and Takeuci, M., et al., (1996) J. Molecular Catalysis A: Chemical 113, 51-57. For TNT and nitro-compounds complex with porphyrins, see Wang, X., et al., (1998) J. Org. Chem 63, 356-360. It is also reported that TNT and its hydrolysis product analogs can be detected using a fluor via evanescent wave in optical fiber, see Takeuci, M., et al. supra.

Infra red studies have been performed on SAM and SAW devices to detect DIMP, see Weber, L., et al., (1994) J. Am. Chem. Soc. 116, 2400-2408. Fluorescence measurements have been used for the detection of chloramphenical, see Cooke, P. R., et al., (1994) J. Chem. Soc. Perkins Trans. 1, 1913-1923, and for the detection of 2, 4-D, see Martinez-Lorente, M. A., et al., (1996) J. Molecular Catalysis A: Chemical 113, 343-353 and Gold, A., et al., (1997) J. Molecular Catalysis A: Chemical 125, 23-32.

Other MIPS utilize a fluor for detection of cAMP, see Meunier, B., et al., (1997) Accounts of Chemical Research 30, 470-476; of sialic acid, see Maldotti, A., et al., (1996) 35, 1126-1131; of fructose, see Hampton, K. W., et al., (1996) J. Molecular Catalysis A: Chemical 113, 167-174; of 2, 4-D, see Bhyrappa, P., et al., (1996) J. Molecular Catalysis A: Chemical 113, 109-116; and -acetyitryptophanamide, see Kamp, Y. W. J., et al., (1996) J. Molecular Catalysis A: Chemical 113, 131-145, the latter using fluorescein in a sol-gel glass imprint.

The binding of different organic molecules to the porphyrins is considered to cause different spectral shifts in the absorbance spectrum of calorimetric molecules such as the porphyrins. Different organics should yield different wavelength shifts. Because the absorbing wavelengths (as well as the energy levels of the electrons) are altered, the wavelengths of the fluorescent light emitted at a longer wavelength are also affected. Thus, the optical spectrum of a MIPS impregnated with a colorimetric agent can clearly be used to corroborate detection and identification of certain sought-after agents.

A porphyrin layered surface of a voltage controlled Fabry Perot cavity is considered herein. As a result, both the mass of the molecules that bind to the cavity surface or the spectral absorption of the porphyrins on the surface of the Fabry Perot cavity can be determined. Colorimetric indicators incorporated into a molecularly imprinted surface of a Fabry Perot cavity permit the specificity of the bound agent to be indicated by the optical spectrum of the colorimetric compound. The amount bound is determined from the mass or optical absorption shift changes as well as from the intensity of the spectral response. As a result, a corroboration of both identity and quantity is obtainable.

Referring again to FIG. 1A, optical source 12 provides the optical stimulus to excite the Fabry-Perot (FP) cavity 14. The FP cavity and/or optical source can be swept to find "valleys" and valley shifts in absorption spectrum associated with porphyrins layer 34 on the top plate of the cavity. In one mode, the optical source can be "broadband" and the FP cavity swept. In a second mode, the optical source can be "stepped" and the FP cavity swept. While other operational modes exists, in all cases doing a pre and post exposure sweep of the porphyrins layer response results in a desirable differential measurement.

Another mode includes differential FP cavities were one cavity is used as a reference to remove common modes effects associated with the optical source while at the same time generating differential responses associated with the porphyrins spectrum shift. A differential measuring technique is disclosed in U.S. Pat. No. 6,550,330. It is also potentially possible to use porphyrin fluorescence to stimulate the cavity with secondary emissions.

The response of the FP cavity to the combined effect of the porphyrins after optical stimulation is measure by integral photosensor 26. Pre agent exposure, the FP cavity in conjunction with the porphyrin response will create a notch in the spectrum as processed by processor 32, which will shift in a prescribed manner after exposure. The depth of the spectral response notch is a measure of species concentration.

The output of the photosensor 26 is used in conjunction with processor 32 to control or conform the FP cavity resonance frequency as well as measure the spectrum and intensity of system output. Determination of the specific chemicals associated with the resulting spectrum shift is thereby made possible.

As the FP cavity is a half wave resonant structure, the optical source may be a band limited and/or a tunable and monochromatic source, e.g. a laser. For example, the visible spectrum is generally accepted to have a range of approximately 35 to 75 nm. If a FP cavity were stimulated at 35 nm it would also be responsive at odd multiples or 35 nm, for example, 105 nm, 165 nm, etc. As a result, a "broadband" optical source spectrally limited to less than 105 mm could be used.

Using suitable photo lithographic techniques, arrays of the described FP cells can be fabricated wherein each FP cavity of the array is sensitive to specific porphyrins. This permits the fabrications of olfactory arrays that can be used at ports of entry so that drugs, explosives, and other agents of interest can be monitored and controlled. The fact that porphyrin sensitivity is reported to be as high 30 to 50 parts per billion suggests that land mine detection is also feasible.

Figure 2:
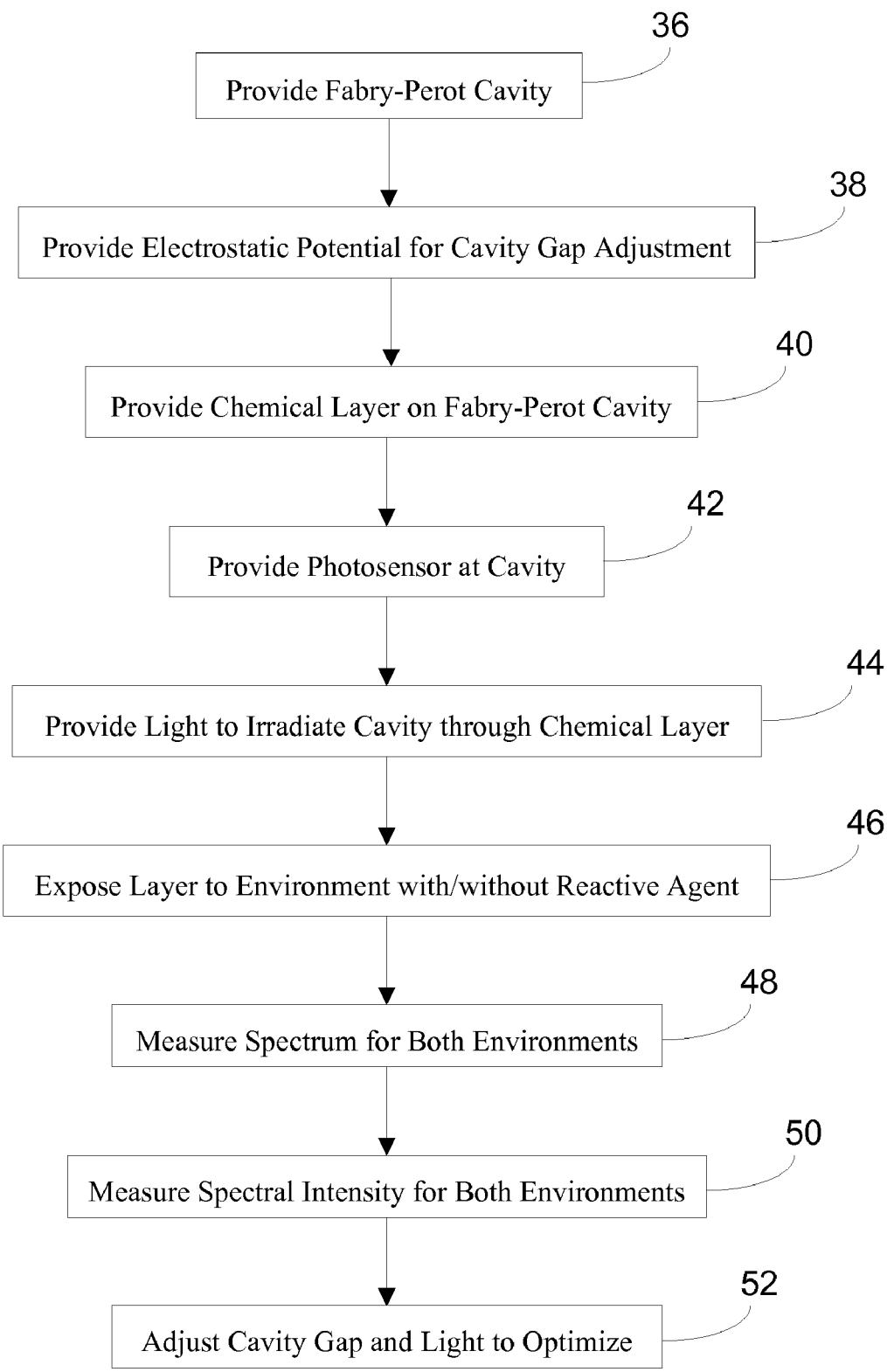
FIG. 2 is a flow-chart of a representative sensing technique.

FIG. 2 illustrates a representative sensing technique according to the description provided herein.

Block 36 represents providing a Fabry-Perot cavity, including pair of partially transmissive, partially reflective, surfaces wherein a first of the surfaces is flexibly suspended adjacent and parallel to a second of the surfaces so that a gap exists therebetween.

Block 38 represents providing a source of variable electrostatic potential for providing a selected electrostatic potential between the first and second surfaces so that the gap is adjustable.

Block 40 represents providing a translucent chemical layer on the flexibly suspended first surface.

Block 42 represents providing a photosensor attached to the second surface outside of the gap.

Block 44 represents providing a source of light. The light irradiates the photosensor through the chemical layer and the first and second surfaces wherein the light is also partially reflected between the surfaces.

Block 46 represents providing a sensing environment wherein an agent undergoes a reaction with the chemical layer. A sensing environment wherein the reaction does not occur is also presented.

Block 48 represents measuring a change in spectrum of an output of the photosensor between the sensing condition wherein the chemical layer undergoes a reaction with the agent of interest and the sensing condition wherein this reaction does not occur.

Block 50 represents measuring a change in spectral intensity of the output of the photosensor between the sensing condition wherein the chemical layer undergoes the reaction with the agent of interest and the sensing condition wherein this reaction does not occur.

Block 52 represents adjusting the gap and the light to provide a desired output of the photosensor.

Obviously, many modifications and variations are possible in light of the above description. It is therefore to be understood that within the scope of the claims the invention may be practiced otherwise than as has been specifically described.

What is claimed is:

1. A sensing method comprising the steps of:

providing a Fabry-Perot cavity, including a pair of partially transmissive, partially reflective, surfaces wherein a first of said surfaces is flexibly suspended adjacent and parallel to a second of said surfaces so that a gap exists therebetween;

providing a source of variable electrostatic potential for providing a selected electrostatic potential between said first and second surfaces so that said gap is adjustable;

providing a translucent chemical layer on said flexibly suspended first surface outside of said gap;

providing a photosensor attached to said second surface outside of said gap; and providing a source of light, said light for irradiating said photosensor through said chemical layer and said first and second surfaces wherein said light is also partially reflected between said surfaces;

providing a sensing environment wherein an agent undergoes a reaction with said chemical layer and a reference environment wherein said reaction does not occur;

measuring a change in spectrum of an output of said photosensor between said sensing environment and said reference environment; and measuring a change in spectral intensity of said output of said photosensor between said sensing environment and said reference environment;

wherein said gap and said light are selected to provide a desired output of said photosensor.

2. The sensing method according to claim 1 wherein said steps of providing a Fabry-Perot cavity;

providing a source of variable electrostatic potential;

providing a translucent chemical layer;

providing a photosensor;

providing a source of light;

measuring a change in spectrum; and measuring a change in spectral intensity are provided on an integrated circuit.

3. A sensing method comprising the steps of:

providing a Fabry-Perot cavity, including a pair of partially transmissive, partially reflective, surfaces wherein a first of said surfaces is flexibly suspended adjacent and parallel to a second of said surfaces so that a gap exists therebetween;

providing a source of variable electrostatic potential for providing a selected electrostatic potential between said first and second surfaces so that said gap is adjustable;

providing a translucent porphyrin layer on said flexibly suspended first surface outside of said gap;

providing a photosensor attached to said second surface outside of said gap; and providing a source of light, said light for irradiating said photosensor through said porphyrin layer and said first and second surfaces wherein said light is also partially reflected between said surfaces;

providing a sensing environment wherein an agent undergoes a reaction with said porphyrin and a reference environment wherein said reaction does not occur;

measuring a change in spectrum of an output of said photosensor between said sensing environment and said reference environment; and measuring a change in spectral intensity of said output of said photosensor between said sensing environment and said reference environment;

wherein said gap and said light are selected to provide a desired output of said photo sensor.

4. The sensing method according to claim 3 wherein said steps of
- providing a Fabry-Perot cavity;
- providing a source of variable electrostatic potential;
- providing a translucent porphyrin layer;
- providing a photosensor;
- providing a source of light;
- measuring a change in spectrum; and
- measuring a change in spectral intensity are provided on an integrated circuit.

5. The method of claim 3 wherein said first partially transmissive, partially reflective, surface is a gold surface.

6. The method of claim 3 wherein said photosensor is a photodiode.

7. The method of claim 3 wherein said source of light is a laser.

8. The method of claim 7 wherein said laser is band limited laser.

9. The method of claim 7 wherein said laser is of a variable wavelength.

10. An optical chemical sensor comprising:
- a Fabry-Perot cavity, wherein the Fabry-Perot cavity comprises first and second partially transmissive, partially reflective, surfaces wherein the first surface is flexibly suspended adjacent and parallel to the second surface so that a gap exists therebetween;
- a source of variable electrostatic potential configured to provide a selected electrostatic potential between said first and second surfaces so that said gap is adjustable;
- a translucent chemical layer on said first surface outside of said gap;
- a photosensor attached to said second surface outside of said gap; and
- a source of light, said light source configured to irradiate said photosensor through said chemical layer and said first and second surfaces wherein said light is also partially reflected between said surfaces.

11. The optical chemical sensor of claim 10, further comprising:
- a sensing environment wherein an agent undergoes a reaction with said chemical layer; and
- a reference environment wherein said reaction does not occur.

12. The optical chemical sensor of claim 11, wherein the Fabry-Perot cavity, the source of variable electrostatic potential, the translucent chemical layer, the photosensor, the source of light, the sensing environment, and the reference environment are provided on an integrated circuit.

13. The optical chemical sensor of claim 12, wherein the translucent chemical layer is porphyrin.

14. The optical chemical sensor of claim 12, wherein the translucent chemical layer is metalloporphyrin.

15. The optical chemical sensor of claim 11, wherein the first partially transmissive, partially reflective, surface is a gold surface.

16. The optical chemical sensor of claim 15, wherein the photosensor is a photodiode.

17. The optical chemical sensor of claim 16, wherein the source of light is a laser.

18. The optical chemical sensor of claim 17, wherein the laser is band limited laser.

19. The optical chemical sensor of claim 18, wherein the laser is of a variable wavelength.

* * * * *